US010045796B2

(12) United States Patent
Powers et al.

(10) Patent No.: US 10,045,796 B2

(45) Date of Patent: Aug. 14, 2018

(54) SPINAL CORRECTION SYSTEM AND METHOD

(71) Applicant: Warsaw Orthopedic, Inc., Warsaw, IN (US)

(72) Inventors: Alison G. Powers, Memphis, TN (US); Chris Johnson, Germantown, TN (US); Timothy S. Oswald, Kennesaw, GA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 242 days.

(21) Appl. No.: 14/965,412

(22) Filed: Dec. 10, 2015

(65) Prior Publication Data

US 2016/0095630 A1 Apr. 7, 2016

Related U.S. Application Data

(63) Continuation of application No. 13/785,969, filed on Mar. 5, 2013, now Pat. No. 9,237,907.

(51) Int. Cl.

| | |
|---|---|
| ***A61B 17/88*** | (2006.01) |
| ***A61B 17/70*** | (2006.01) |
| *A61B 17/00* | (2006.01) |

(52) U.S. Cl.

CPC ........ *A61B 17/7019* (2013.01); *A61B 17/705* (2013.01); *A61B 17/7022* (2013.01); *A61B 17/7031* (2013.01); *A61B 17/7044* (2013.01); *A61B 17/7049* (2013.01); *A61B 17/7059* (2013.01); *A61B 17/701* (2013.01); *A61B 17/7004* (2013.01); *A61B 2017/00004* (2013.01)

(58) Field of Classification Search

CPC ................ A61B 17/70; A61B 17/7002; A61B 17/7019; A61B 17/702; A61B 17/7049; A61B 17/705; A61B 17/7053

USPC ......................... 606/250–253, 260, 278, 279

See application file for complete search history.

(56) References Cited

U.S. PATENT DOCUMENTS

| | | | | |
|---|---|---|---|---|
| 6,551,320 B2 | 4/2003 | Lieberman | A61B 17/7022 606/263 |
| 6,565,569 B1 | 5/2003 | Assaker | A61B 17/7037 606/250 |
| 8,414,616 B2 | 4/2013 | Berrevoets | A61B 17/7044 606/250 |
| 2006/0264935 A1 | 11/2006 | White | A61B 17/7031 606/257 |
| 2007/0233073 A1 | 10/2007 | Wisnewski et al. | 606/61 |

(Continued)

*Primary Examiner* — Ellen C Hammond
*Assistant Examiner* — Christina Negrellirodrigue

(57) ABSTRACT

A spinal correction system comprises a first member configured for attachment to a first portion of vertebral tissue and a second member is configured for attachment to a second portion of the vertebral tissue spaced from the first portion. A third member has a non-flexible configuration relative to the first and second members and is configured for attachment to an apical portion of the vertebral tissue and along at least a portion of at least two vertebrae. The third member extends between a first end connected to the first member at a first transition configured for attachment to the first vertebral tissue and a second end connected to the second member at a second transition configured for attachment to the vertebral tissue. Methods of use are disclosed.

20 Claims, 5 Drawing Sheets

(56) References Cited

U.S. PATENT DOCUMENTS

| | | | | |
|---|---|---|---|---|
| 2008/0058805 | A1 | 3/2008 | Stuart | A61B 17/7005 606/914 |
| 2008/0086126 | A1 | 4/2008 | Miller | A61B 17/705 606/86 R |
| 2008/0262553 | A1 | 10/2008 | Hawkins | A61B 17/705 606/278 |
| 2009/0222042 | A1 | 9/2009 | Firkins | A61B 17/701 606/246 |
| 2010/0217319 | A1 | 8/2010 | Todd | A61B 17/705 606/246 |
| 2010/0222821 | A1* | 9/2010 | Bowden | A61B 17/7011 606/260 |
| 2011/0264145 | A1 | 10/2011 | Farris | 606/278 |
| 2011/0301644 | A1 | 12/2011 | Belliard | A61B 17/7008 606/263 |
| 2013/0268005 | A1 | 10/2013 | Rezach et al. | 606/263 |

* cited by examiner

SPINAL CORRECTION SYSTEM AND METHOD

CROSS REFERENCE TO RELATED APPLICATIONS

This application is a continuation of U.S. patent application Ser. No. 13/785,969, filed on Mar. 5, 2013, which is expressly incorporated herein by reference, in its entirety.

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, for stabilization of a treated section of a spine. This disclosure describes an improvement over these prior art technologies.

SUMMARY

Accordingly, a spinal correction construct is provided. The spinal correction construct comprises a first member configured for attachment to a first portion of vertebral tissue. A second member is configured for attachment to a second portion of the vertebral tissue spaced from the first portion. A third member includes a non-flexible configuration relative to the first and second members. The third member is configured for attachment to an apical portion of the vertebral tissue and along at least a portion of at least two vertebrae. The third member extends between a first end and a second end. The first end is connected to the first member at a first transition and is configured for attachment to the first vertebral tissue. The second is end connected to the second member at a second transition and is configured for attachment to the second vertebral tissue.

BRIEF DESCRIPTION OF THE DRAWINGS

The present disclosure will become more readily apparent from the specific description accompanied by the following drawings, in which.

DETAILED DESCRIPTION

Figure 2:
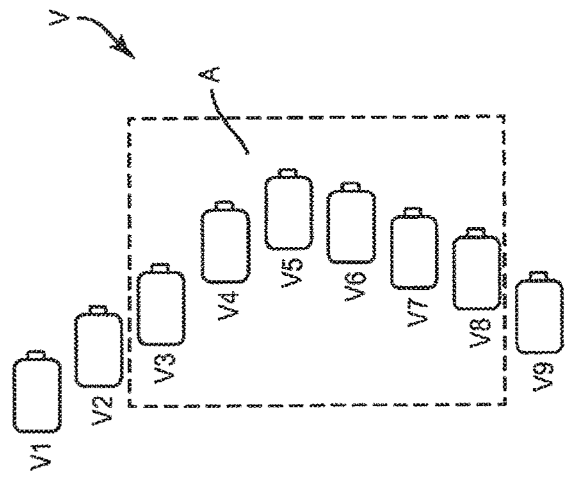
FIG. 2 is a plan view of vertebrae.

The exemplary embodiments of the spinal correction system and related methods of use are discussed in terms of medical devices for the treatment of musculoskeletal disorders. In some embodiments, the spinal correction system may be employed in applications for correction of deformities, such as scoliosis, with a device for applying a constant load to a flexible longitudinal element.

In one embodiment, an apical fusion system is provided with adjacent level tethering. In one embodiment, the system includes a less-fusion device employed with a method for scoliosis correction utilizing the growth of a child for continuous correction. In one embodiment, an apex of a curve, for example, including three vertebral levels and/or intervertebral disc space is fused with a spinal rod. In some embodiments, the system tethers adjacent vertebral levels. In one embodiment, the system includes a transition from a non-deformable longitudinal member, for example, a metal spinal rod or a PEEK spinal rod for fusion, to a deformable member, for example, a polymer member, an autograft member, an allograft member, and/or a flexible metal member. The transition is disposed at one vertebral body, on opposite sides, for example, anterior and posterior. In some embodiments, the system includes a device employed with a method for scoliosis correction utilizing part fusion/part fusionless for pediatric patients, and can be used for more aggressive curves.

In one embodiment, an apical fusion system is provided that includes a non-deformable member, a first deformable member, a second deformable member, a first transition and a second transition. In some embodiments, the non-deformable member provides rigid fixation to vertebrae. In one embodiment, an apical fusion system provides adjacent level tethering. In one embodiment, the system includes a rod attached to a tether. In one embodiment, the system includes a rigid rod fixed to a fusion section of vertebrae and a deformable tether. In one embodiment, the rod is fixed to vertebrae via a bone fastener. In one embodiment, the system provides apical fusion at two or more vertebral bodies. In one embodiment, tethering occurs at two or more vertebral levels.

In one embodiment, the system includes at least two rods connected to at least one tether. In some embodiments, the rods and tether can be separately attached, integrally connected or formed as a single piece. In one embodiment, the tether can be contained within at least one plate and/or within at least one rod for permanent fixation of the system with vertebrae. In one embodiment, the at least one tether can be contained within at least one rod. In one embodiment, two tethers can be inserted into two hollow rods. In one embodiment, at least one tether can be attached to a rod. In one embodiment, the rod comprises internal threading at an end that matingly engages with a tether. In some embodiments, the mating ends of the rod and tether comprise a metal. In one embodiment, at least one tether is non-permanently fixed to a plate via a set screw.

In one embodiment, the system includes a single rod attached to at least one tether. In one embodiment, the system includes a double plate and bone fasteners. In some embodiments, the bone fasteners are inserted into openings in the plate and the rod is set within the head of one of the bone fasteners. In some embodiments, a set screw fixes the rod with the bone fastener. In some embodiments, the tether is set within the head of one of the bone fasteners and a set screw fixes the tether with the bone fastener. In one embodiment, the system includes a single plate and a bone fastener.

In one embodiment, an apical fusion system is provided that is positioned on the lumbar region of the spine. In one embodiment, the system is configured to be positioned either anteriorly or posteriorly. In one embodiment, the system is configured for bilateral fusion.

In one embodiment, the system includes a posterior dual rod fusion portion and a posterior tether. In one embodiment, the tether is fixed to a convex side of a vertebral curve. In one embodiment, the system includes a posterior dual rod fusion portion and a posterior tether disposed along a costo-vertebral space, a transverse process/rib junction adjacent a costo-vertebral space and/or a costo-transverse ligament.

In some embodiments, one or all of the components of the spinal correction system may be disposable, peel-pack, pre-packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal correction system in accordance with the principles of the present disclosure. Alternate embodiments are also disclosed. Reference will now be made in detail to the exemplary embodiments of the present disclosure, which are illustrated in the accompanying figures. Turning to FIGS. 1-5, there are illustrated components of a system, such as, for example, a spinal correction system 20, in accordance with the principles of the present disclosure.

The components of spinal correction system 20 can be fabricated from biologically acceptable materials suitable for medical applications, including metals, synthetic polymers, ceramics, bone material, tissue and/or their composites, depending on the particular application and/or preference of a medical practitioner. For example, the components of spinal correction system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening elements and/or instruments, as described herein.

System 20 is employed, for example, with an open, mini-open or minimally invasive surgical technique to attach one or a plurality of longitudinal elements to a first side, such as, for example, a convex side of a spine that has a spinal disorder. In one embodiment, the longitudinal element(s), such as, for example, a tether and/or a spinal rod, may be affixed to the convex side of each of a plurality of vertebrae such that system 20 prevents growth of vertebrae of a selected section of the spine while allowing for growth and adjustments to a second side, such as, for example, a concave side of the plurality of vertebrae for a correction treatment to treat various spine pathologies, such as, for example, adolescent idiopathic scoliosis and Scheuermann's kyphosis.

Spinal correction system 20 includes a member, such as, for example, a tether 22 configured for attachment to a first portion of vertebral tissue, such as, for example, a selected section of vertebrae, as discussed herein. Tether 22 comprises a flexible longitudinal element, as described herein, which extends between an end 24 and an end 26. Tether 22 defines a longitudinal axis upon disposal in a linear orientation.

In some embodiments, all or only a portion of tether 22 may have flexible properties, such as the flexible properties corresponding to the material examples described above, such that tether 22 provides a selective amount of expansion and/or extension in an axial direction. In some embodiments, all or only a portion of tether 22 may have a semi-rigid, rigid or elastic configuration, and/or have elastic properties, such as the elastic properties corresponding to the material examples described above, such that tether 22 provides a selective amount of expansion and/or extension in an axial direction.

In some embodiments, tether 22 has a flexible configuration, which includes movement in a lateral or side to side direction and prevents expanding and/or extension in an axial direction upon fixation with vertebrae. In some embodiments, tether 22 may be compressible in an axial direction. Tether 22 can include a plurality of separately attachable or connectable portions or sections, such as bands or loops, or may be monolithically formed as a single continuous element.

Tether 22 can have a uniform thickness/diameter. In some embodiments, tether 22 may have various surface configurations, such as, for example, rough, threaded for connection with surgical instruments, arcuate, undulating, porous, semi-porous, dimpled, polished and/or textured according to the requirements of a particular application. In some embodiments, the thickness defined by tether 22 may be uniformly increasing or decreasing, or have alternate diameter dimensions along its length. In some embodiments, tether 22 may have various cross section configurations, such as, for example, oval, oblong, triangular, rectangular, square, polygonal, irregular, uniform, non-uniform, variable and/or tapered.

In some embodiments, tether 22 may have various lengths, according to the requirements of a particular application. In some embodiments, tether 22 may be braided, such as a rope, or include a plurality elongated elements to provide a predetermined force resistance. In some embodiments, tether 22 may be made from autograft and/or allograft, as described above, and be configured for resorbable or degradable applications. In one embodiment, tether 22 is a cadaver tendon. In one embodiment, tether 22 is a tendon that may be harvested, for example, from a patient or donor. In some embodiments, a tendon harvested from a patient may be affixed in remote locations with the patient's body.

A tether 28, similar to tether 22, extends between an ends 30, 32 and is configured for attachment to a first portion of vertebral tissue, such as, for example, a selected section of vertebrae, as discussed herein. Tether 28 is configured for attachment to a selected section of vertebrae spaced from the selected section of vertebrae connected to tether 22. Tether 28 defines a longitudinal axis upon disposal in a linear orientation. In some embodiments, the selected sections of vertebrae may be adjacent, staggered and/or offset. In some embodiments, tether 28 can have varying degrees of flexibility relative to tether 22.

A member, such as, for example, a spinal rod 34 extends between ends 36, 38 and has a non-flexible configuration relative to each of tethers 22, 28. Spinal rod 34 is configured for attachment to an apical portion of vertebral tissue and along at least a portion of a first vertebra and a second vertebra, as described herein. Spinal rod 34 is configured for disposal with vertebrae intermediate tethers 22, 28. In some embodiments, intermediate disposal of spinal rod 34 can include co-axial, offset, staggered, transverse, angular and/or relative posterior/anterior orientations with tethers 22, 28. Spinal rod 34 defines a longitudinal axis upon disposal in a linear orientation.

In some embodiments, spinal rod 34 has a rigid and/or non-flexible configuration relative to tether 22 and/or tether 28 such that all or only a portion of spinal rod 34 may have a semi-rigid, rigid or elastic configuration, and/or have elastic properties, such as the elastic properties corresponding to the material examples described above. In some embodiments, spinal rod 34 provides a selective amount of expansion and/or extension in an axial direction. In some embodiments, spinal rod 34 has a flexible configuration, which includes movement in a lateral or side to side direction and prevents expanding and/or extension in an axial direction upon fixation with vertebrae. In some embodiments, spinal rod 34 may be compressible in an axial direction. Spinal rod 34 can include a plurality of separately attachable or connectable portions or sections, or may be monolithically formed as a single continuous element. System 20 can include one or a plurality of spinal rods 34. In some embodiments, spinal rod 34 is configured to extend over a plurality of vertebral levels.

Spinal rod 34 can have a uniform thickness/diameter. In some embodiments, spinal rod 34 may have various surface configurations, such as, for example, rough, threaded for connection with surgical instruments, arcuate, undulating, porous, semi-porous, dimpled, polished and/or textured according to the requirements of a particular application. In some embodiments, the thickness defined by spinal rod 34 may be uniformly increasing or decreasing, or have alternate diameter dimensions along its length. In some embodiments, spinal rod 34 may have various cross section configurations, such as, for example, oval, oblong, triangular, rectangular, square, polygonal, irregular, uniform, non-uniform, variable and/or tapered.

A transition, such as, for example, a plate 40 includes bone fasteners 42, 44 configured for fixation with vertebrae. Plate 40 has a substantially rectangular configuration. In some embodiments, plate 40 can be variously configured, such as, for example, tubular, oval, oblong, triangular, square, polygonal, irregular, uniform, non-uniform, variable, hollow and/or tapered. In some embodiments, plate 40 can have alternate cross-section and/or thickness configurations, such as, arcuate, undulating, offset, staggered, tubular, oval, oblong, triangular, square, polygonal, irregular, uniform, variable, hollow and/or tapered. In some embodiments, plate 40 may include alternate surface configurations, such as, for example, friction, rough, arcuate, undulating, mesh, porous, semi-porous, dimpled and/or textured according to the requirements of a particular application.

Plate 40 has a double plate configuration and includes an opening 46 configured for disposal of bone fastener 42 and an opening 48 configured for disposal of bone fastener 44. Opening 46 is spaced from opening 48 along the surface of plate 40 for alignment with tether 22, tether 28 and/or spinal rod 34, according to the requirements of a particular application. Openings 46, 48 are substantially circular and extend through the thickness of plate 40. In some embodiments, opening 46 and/or opening 48 can be variously configured, such as, for example, oval, oblong, triangular, square, polygonal, irregular, uniform, non-uniform and/or tapered.

Figure 3:
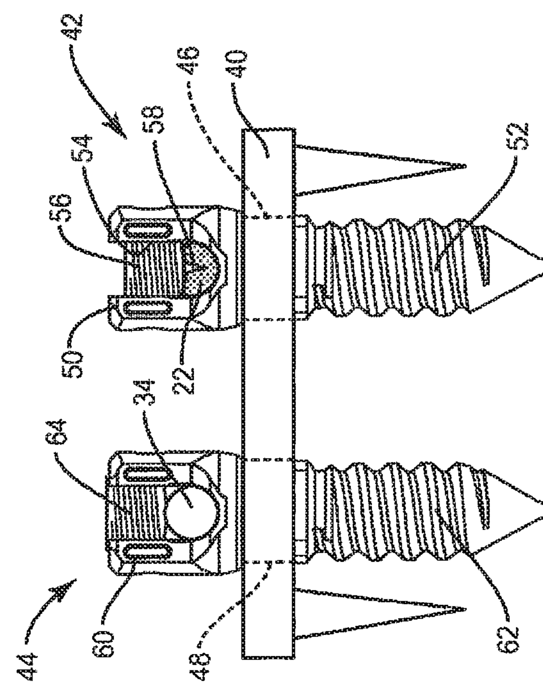
FIG. 3 is a side view of components of the system shown in FIG. 1.

Opening 46 is configured to receive bone fastener 42 that connects tether 22 to plate 40 and/or tissue, as will be described. Bone fastener 42 has a length that is extendable along a longitudinal axis. Bone fastener 42 comprises a head 50 and an elongated shaft 52 configured for penetrating tissue, as shown in FIG. 3.

Shaft 52 has a cylindrical cross section configuration and includes an outer surface having an external thread form. In some embodiments, the external thread form may include a single thread turn or a plurality of discrete threads. In some embodiments, other engaging structures may be located on shaft 52, such as, for example, a nail configuration, barbs, expanding elements, raised elements and/or spikes to facilitate engagement of shaft 52 with tissue, such as, for example, vertebrae.

In some embodiments, all or only a portion of the shaft 52 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 52 may include one or a plurality of openings. In some embodiments, all or only a portion of the outer surface of shaft 52 may have alternate surface configurations to enhance fixation with tissue such as, for example, rough, arcuate, undulating, mesh, porous, semi-porous, dimpled and/or textured according to the requirements of a particular application. In some embodiments, all or only a portion of shaft 52 may be disposed at alternate orientations, relative to the longitudinal axis, such as, for example, transverse, perpendicular and/or other angular orientations such as acute or obtuse, co-axial and/or may be offset or staggered. In some embodiments, that all or only a portion of shaft 52 may be cannulated.

Head 50 includes a pair of spaced apart arms having an inner surface that defines a U-shaped passageway 54. Passageway 54 is configured for disposal of an implant, such as, for example, tether 22. In some embodiments, all or only a portion of passageway 54 may have alternate cross section configurations, such as, for example, oval, oblong, triangular, square, polygonal, irregular, uniform, non-uniform, offset, staggered, and/or tapered. In some embodiments, the arms of head 50 may be disposed at alternate orientations, relative to the longitudinal axis, such as, for example, transverse, perpendicular and/or other angular orientations such as acute or obtuse, co-axial and/or may be offset or staggered.

The inner surface of head 50 includes a thread form configured for engagement with a coupling member, such as, for example, a set screw 56. Screw 56 is threadably engageable with the inner surface of head 50 to connect, attach, fix and/or lock, provisionally, removably and/or permanently, tether 22 to plate 40 and/or tissue, as will be described. Screw 56 includes an element 58 that penetrates tether 22 to facilitate connection of the components of system 20 and tissue.

Opening 48 is configured to receive bone fastener 44 that connects spinal rod 34 to plate 40 and/or tissue, as will be described. Bone fastener 44 has a length that is extendable along a longitudinal axis. Bone fastener 44, similar to bone fastener 42, comprises a head 60 and an elongated shaft 62 configured for penetrating tissue, as shown in FIG. 3. The inner surface of head 60 includes a thread form configured for engagement with a coupling member, such as, for example, a set screw 64. Set screw 64 is threaded with head 60 to connect, attach, fix and/or lock, provisionally, removably and/or permanently, spinal rod 34 to plate 40 and/or tissue, as will be described.

A transition, such as, for example, a plate 66, similar to plate 40, includes bone fasteners 68, 70 configured for fixation with vertebrae. Plate 66 has a double plate configuration and includes an opening 72 configured for disposal of bone fastener 68 and an opening 74 configured for disposal of bone fastener 70. Opening 72 is spaced from opening 74 along the surface of plate 66 for alignment with tether 22, tether 28 and/or spinal rod 34, according to the requirements of a particular application.

Opening 72 is configured to receive bone fastener 68 that connects tether 28 to plate 66 and/or tissue, as will be described. Bone fastener 68 has a length that is extendable along a longitudinal axis. Bone fastener 68, similar to bone fastener 42, comprises a head 76 and an elongated shaft (not shown) configured for penetrating tissue.

Head 76 includes a pair of spaced apart arms having an inner surface that defines a U-shaped passageway configured for disposal of an implant, such as, for example, tether 28. The inner surface of head 76 includes a thread form configured for engagement with a coupling member, such as, for example, a set screw 78, similar to screw 56. Screw 78 is threadably engageable with the inner surface of head 76 to connect, attach, fix and/or lock, provisionally, removably and/or permanently, tether 28 to plate 66 and/or tissue, as will be described.

Opening 74 is configured to receive bone fastener 70 that connects spinal rod 34 to plate 66 and/or tissue, as will be described. Bone fastener 70 has a length that is extendable along a longitudinal axis. Bone fastener 70, similar to bone fastener 44, comprises a head 80 and an elongated shaft (not shown) configured for penetrating tissue. The inner surface of head 80 includes a thread form configured for engagement with a coupling member, such as, for example, a set screw 82, similar to set screw 64. Set screw 82 is threaded with head 80 to connect, attach, fix and/or lock, provisionally, removably and/or permanently, spinal rod 34 to plate 66 and/or tissue, as will be described.

Figure 5:
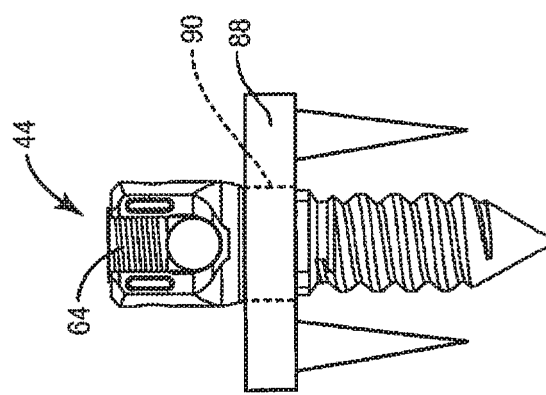
FIG. 5 is a side view of components of the system shown in FIG. 1.
Figure 4:
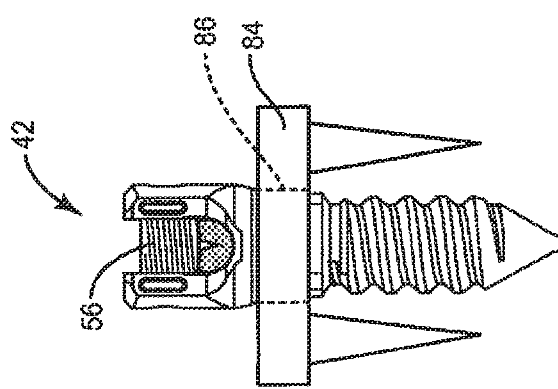
FIG. 4 is a side view of components of the system shown in FIG. 1.

A plate 84, as shown in FIG. 4, has a single plate configuration and includes an opening 86 configured for disposal of bone fastener 42, described herein, to connect, attach, fix and/or lock, provisionally, removably and/or permanently, tether 22 to tissue, as will be described. A plate 88, as shown in FIG. 5, has a single plate configuration and includes an opening 90 configured for disposal of bone fastener 44, described herein, to connect, attach, fix and/or lock, provisionally, removably and/or permanently, spinal rod 34 to tissue, as will be described. A plate 92 has a single plate configuration and includes an opening 94 configured for disposal of bone fastener 68, described herein, to connect, attach, fix and/or lock, provisionally, removably and/or permanently, tether 28 to tissue, as will be described.

In some embodiments, spinal correction system 20 can include one or a plurality of fasteners, such as those described herein and/or fixation elements, which may be employed with a single vertebral level or a plurality of vertebral levels. In some embodiments, the fasteners may be engaged with vertebrae in various orientations, such as, for example, series, parallel, offset, staggered and/or alternate vertebral levels. In some embodiments, the fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. These bone fasteners and/or fixation elements may be coated with an osteoinductive or osteoconductive material to enhance fixation, and/or include one or a plurality of therapeutic agents.

In assembly, operation and use, spinal correction system 20, similar to the system described above, is employed with a surgical procedure, such as, for a correction treatment to treat adolescent idiopathic scoliosis and/or Scheuermann's kyphosis of a spine. In some embodiments, one or all of the components of spinal correction system 20 can be delivered or implanted as a pre-assembled device or can be assembled in situ. Spinal correction system 20 may be completely or partially revised, removed or replaced.

Figure 1:
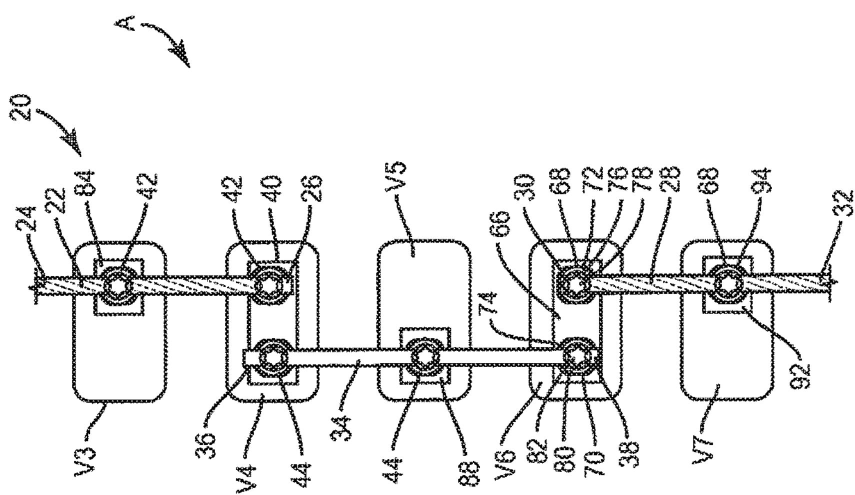
FIG. 1 is a plan view of components of one embodiment of a spinal correction system in accordance with the principles of the present disclosure disposed with vertebrae.

For example, as shown in FIGS. 1 and 2, spinal correction system 20 can be employed with a surgical correction treatment of an applicable condition or injury of an affected section of a spinal column and adjacent areas within a body, such as, for example, vertebrae V1-V9 of vertebrae V. In some embodiments, spinal correction system 20 may be employed with one or a plurality of vertebrae.

In use, to treat a selected section of vertebrae V, which includes an apical portion A of vertebrae V, a medical practitioner obtains access to a surgical site including vertebrae V in any appropriate manner, such as through incision and retraction of tissues. In some embodiments, spinal correction system 20 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 20. A preparation instrument (not shown) can be employed to prepare tissue surfaces of vertebrae V, as well as for aspiration and irrigation of a surgical region according to the requirements of a particular surgical application.

Pilot holes are made in vertebrae V for receiving bone fasteners 42, 44, 68, 70 that connect plates 40, 66, 84, 88, 92, tethers 22, 28 and spinal rod 34 with vertebrae V1-V9. In some embodiments, the sequence and/or order of connecting bone fasteners 42, 44, 68, 70, plates 40, 66, 84, 88, 92, tethers 22, 28 and spinal rod 34 with vertebrae V1-V9, may be variously arranged.

For example, a pilot hole is made in vertebra V3 for receiving bone fastener 42 that connects tether 22 and plate 84 with vertebra V3. Plate 84 is removably engaged with a delivery instrument (not shown) and delivered along the surgical pathway. Plate 84 is delivered to a surgical site adjacent vertebra V3. Plate 84 is oriented for fixation with vertebra V3. Bone fastener 42 is inserted or otherwise engaged with vertebra V3 to fix an intermediate portion of tether 22 with plate 84 and vertebra V3. Bone fasteners 42 are similarly inserted or otherwise engaged with vertebrae V1, V2 to fix tether 22 with plates 84 and vertebrae V1, V2.

A pilot hole is made in vertebra V4 for receiving bone fastener 42. The pilot hole in vertebra V4 is disposed to connect tether 22 in a selected alignment with bone fastener 42 attached to vertebra V3 along vertebrae V. Bone fastener 42 connects end 26 of tether 22 and plate 40 with vertebra V4. A pilot hole is made in vertebra V4 for receiving bone fastener 44 and is spaced laterally from the pilot hole for bone fastener 42 in vertebra V4. Bone fastener 44 connects end 36 of spinal rod 34 and plate 40 with vertebra V4. Plate 40 is removably engaged with a delivery instrument (not shown) and delivered along the surgical pathway. Plate 40 is delivered to a surgical site adjacent vertebra V4. Plate 40 is oriented for fixation with vertebra V4. Bone fastener 42 is inserted or otherwise engaged with vertebra V4 to fix end 26 with plate 40 and vertebra V4. Bone fastener 44 is inserted or otherwise engaged with vertebra V4 to fix end 36 with plate 40 and vertebra V4.

A pilot hole is made in vertebra V5 for receiving bone fastener 44. The pilot hole in vertebra V5 is disposed to connect spinal rod 34 in a selected alignment with bone fastener 44 attached to vertebra V4 and/or vertebra V6 along vertebrae V. Bone fastener 44 connects an intermediate portion of spinal rod 34 and plate 88 with vertebra V5. Plate 88 is removably engaged with a delivery instrument (not shown) and delivered along the surgical pathway. Plate 88 is delivered to a surgical site adjacent vertebra V5. Plate 88 is oriented for fixation with vertebra V5. Bone fastener 44 is inserted or otherwise engaged with vertebra V5 to fix an intermediate portion of spinal rod 34 with plate 88 and vertebra V5.

A pilot hole is made in vertebra V6 for receiving bone fastener 70. The pilot hole in vertebra V6 is disposed to connect spinal rod 34 in a selected alignment with bone fastener 44 attached to vertebra V5 along vertebrae V. Bone fastener 70 connects end 38 of spinal rod 34 and plate 66 with vertebra V6. A pilot hole is made in vertebra V6 for receiving bone fastener 68 and is spaced laterally from the pilot hole for bone fastener 70 in vertebra V6. Bone fastener 68 connects end 30 of tether 28 and plate 66 with vertebra V6. Plate 66 is removably engaged with a delivery instrument (not shown) and delivered along the surgical pathway. Plate 66 is delivered to a surgical site adjacent vertebra V6. Plate 66 is oriented for fixation with vertebra V6. Bone fastener 70 is inserted or otherwise engaged with vertebra V6 to fix end 38 with plate 66 and vertebra V6. Bone fastener 68 is inserted or otherwise engaged with vertebra V6 to fix end 30 with plate 66 and vertebra V6.

A pilot hole is made in vertebra V7 for receiving bone fastener 68. The pilot hole in vertebra V7 is disposed to connect tether 28 in a selected alignment with bone fastener 68 attached to vertebra V6 along vertebrae V. Bone fastener 68 connects an intermediate portion of tether 28 and plate 92 with vertebra V7. Plate 92 is removably engaged with a delivery instrument (not shown) and delivered along the surgical pathway. Plate 92 is delivered to a surgical site adjacent vertebra V7. Plate 92 is oriented for fixation with vertebra V7. Bone fastener 68 is inserted or otherwise engaged with vertebra V1 to fix an intermediate portion of tether 28 with plate 92 and vertebra V7. Bone fasteners 68 are similarly inserted or otherwise engaged with vertebrae V8, V9 to fix tether 28 with plates 92 and vertebrae V8, V9.

As shown in FIGS. 1 and 2, spinal rod 34 is attached with apical portion A, and tether 22 and tether 28 are axially spaced along vertebrae V. Tether 22 and tether 28 are disposed in a substantially co-axial arrangement along vertebrae V. Spinal rod 34 and tethers 22, 28 are disposed in a substantially offset and/or staggered arrangement along vertebrae V. In this configuration, the components of spinal correction system 20 are attached with a first side, such as, for example, a convex side of vertebrae V to prevent growth of a selected section of vertebrae V, while allowing for growth and adjustments to a second side, such as, for example, a concave side of vertebrae V to provide treatment. Compression of vertebrae V occurs along the convex side. As forces and/or force changes are applied to spinal correction system 20, such as, for example, patient growth, trauma and degeneration, and/or system 20 component creep, deformation, damage and degeneration, tether 22 and/or tether 28 adapts with a responsive force to maintain the applied force transmitted from the bone fasteners substantially constant.

In one embodiment, spinal correction system 20 includes an agent, which may be disposed, packed or layered within, on or about the components and/or surfaces of spinal correction system 20. For example, the plates can comprise one or a plurality of surface treatments and/or coatings including the agent. In some embodiments, the agent may include bone growth promoting material, such as, for example, bone graft to enhance fixation of the fixation elements with vertebrae V.

In some embodiments, the agent may include therapeutic polynucleotides or polypeptides. In some embodiments, the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of spinal correction system 20 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal correction system 20. Upon completion of the procedure, the surgical instruments, assemblies and non-implant components of spinal correction system 20 are removed from the surgical site and the incision is closed.

In some embodiments, the components of spinal correction system 20 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 20 and method of use may be used to prevent or minimize curve progression in individuals of various ages.

Figure 7:
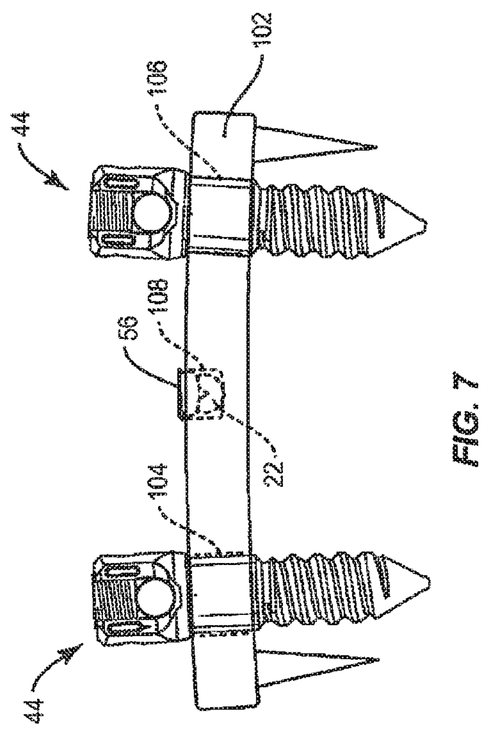
FIG. 7 is a side view of components of the system shown in FIG. 6.
Figure 6:
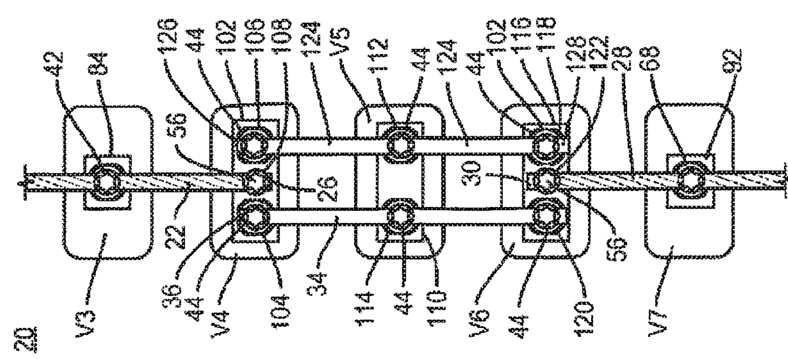
FIG. 6 is a plan view of components of one embodiment of a spinal correction system in accordance with the principles of the present disclosure disposed with vertebrae.

In one embodiment, as shown in FIGS. 6 and 7, spinal correction system 20, similar to the systems and methods described herein, is employed with a surgical correction treatment of an applicable condition or injury of an affected section of a spinal column and adjacent areas within a body, such as, for example, vertebrae V1-V9 of vertebrae V.

Spinal correction system 20 comprises a spinal rod 124, similar to spinal rod 34 described herein, extending between ends 126, 128 and a plate 102, similar to the plates 40, 66 described above, having a double plate configuration and including an opening 104 configured for disposal of bone fastener 44, described herein, and an opening 106 configured for disposal of bone fastener 44. Opening 106 is spaced from opening 104 along the surface of plate 102 for alignment of spinal rods 34, 124 described. Plate 102 includes a cavity 108 configured for disposal of tether 22, described herein. The inner surface of cavity 108 includes a thread form configured for engagement with set screw 56, described herein. Screw 56 is threadably engageable with the inner surface of cavity 108 to connect, attach, fix and/or lock, provisionally, removably and/or permanently, tether 22 with plate 102 to facilitate connection of the components of system 20 and tissue.

A plate 110, similar to the plates 40, 66 described above, has a double plate configuration and includes an opening 112 configured for disposal of bone fastener 44 and an opening 114 configured for disposal of bone fastener 44. Opening 114 is spaced from opening 112 along the surface of plate 110 for alignment spinal rods 34, 124.

A plate 116, similar to the plate 102 described above, has a double plate configuration and includes an opening 118 configured for disposal of bone fastener 44 and an opening 120 configured for disposal of bone fastener 44. Opening 120 is spaced from opening 118 along the surface of plate 116 for alignment of spinal rods 34, 124. Plate 116 includes a cavity 122 configured for disposal of tether 28. The inner surface of cavity 122 includes a thread form configured for engagement with set screw 56 to connect, attach, fix and/or lock, provisionally, removably and/or permanently, tether 28 with plate 116 to facilitate connection of the components of system 20 and tissue.

In use, similar to the methods described herein, pilot holes are made in vertebrae V for receiving bone fasteners 42, 44 that connect plates 84, 102, 110, 116, 92, tethers 22, 28 and spinal rod 34, 124 with vertebrae V1-V9. In some embodiments, the sequence and/or order of connecting bone fasteners 42, 44 plates 84, 102, 110, 116, 92, tethers 22, 28 and spinal rod 34, 124 with vertebrae V1-V9, may be variously arranged.

A pilot hole is made in vertebra V3 for receiving bone fastener 42 that connects tether 22 and plate 84 with vertebra V3. Plate 84 is removably engaged with a delivery instrument (not shown) and delivered along the surgical pathway. Plate 84 is delivered to a surgical site adjacent vertebra V3. Plate 84 is oriented for fixation with vertebra V3. Bone fastener 42 is inserted or otherwise engaged with vertebra V3 to fix an intermediate portion of tether 22 with plate 84 and vertebra V3. Bone fasteners 42 are similarly inserted or otherwise engaged with vertebrae V1, V2 to fix tether 22 with plate 84 and vertebrae V1, V2.

Pilot holes are made in vertebra V4 for receiving bone fasteners 44. The pilot holes in vertebra V4 are disposed to connect rods 34, 124 in an offset alignment with bone fastener 42 attached to vertebra V3 along vertebrae V. Pilot holes are made in vertebra V4 for receiving bone fasteners 44. Bone fasteners 44 connect end 36 of rod 34 and end 126 of rod 124 and plate 102 with vertebra V4. Plate 102 is removably engaged with a delivery instrument (not shown) and delivered along the surgical pathway. Plate 102 is delivered to a surgical site adjacent vertebra V4. Plate 102 is oriented for fixation with vertebra V4. Bone fasteners 44 are inserted or otherwise engaged with vertebra V4 to fix end 26 and end 126 with plate 102 and vertebra V4. End 26 of tether 22 is fixed with plate 102 and connected to vertebra V4.

Pilot holes are made in vertebra V5 for receiving bone fasteners 44. The pilot holes in vertebra V5 are disposed to connect spinal rods 34, 124 in a selected alignment with bone fasteners 44 attached to vertebra V4 and/or vertebra V6 along vertebrae V. Bone fastener 44 connects an intermediate portion of spinal rods 34, 124 and plate 110 with vertebra V5. Plate 110 is removably engaged with a delivery instrument (not shown) and delivered along the surgical pathway. Plate 110 is delivered to a surgical site adjacent vertebra V5. Plate 110 is oriented for fixation with vertebra V5. Bone fasteners 44 are inserted or otherwise engaged with vertebra V5 to fix an intermediate portion of spinal rods 34, 124 with plate 110 and vertebra V5.

Pilot holes are made in vertebra V6 for receiving bone fasteners 44 being spaced laterally apart from each other along vertebrae V6. The pilot holes in vertebra V6 are disposed to connect rods 34, 124 in alignment with bone fasteners 44 attached to vertebra V5 along vertebrae V. Bone fasteners 44 connect end 38 of spinal rod 34, end 128 of spinal rod 124 and plate 116 with vertebra V6. Plate 116 is removably engaged with a delivery instrument (not shown) and delivered along the surgical pathway. Plate 116 is delivered to a surgical site adjacent vertebra V6. Plate 116 is oriented for fixation with vertebra V6. Bone fasteners 44 are inserted or otherwise engaged with vertebra V6 to fix ends 38, 128 with plate 116 and vertebra V6. End 30 of tether 28 is fixed with plate 116 and vertebra V6.

A pilot hole is made in vertebra V7 for receiving bone fastener 68. The pilot hole in vertebra V7 is disposed to connect tether 28 in an offset alignment with bone fasteners 44 attached to vertebra V6 along vertebrae V. Bone fastener 68 connects an intermediate portion of tether 28 and plate 92 with vertebra V7. Plate 92 is removably engaged with a delivery instrument (not shown) and delivered along the surgical pathway. Plate 92 is delivered to a surgical site adjacent vertebra V7. Plate 92 is oriented for fixation with vertebra V7. Bone fastener 68 is inserted or otherwise engaged with vertebra V7 to fix an intermediate portion of tether 28 with plate 92 and vertebra V7. Bone fasteners 68 are similarly inserted or otherwise engaged with vertebrae V8, V9 to fix tether 28 with plates 92 and vertebrae V8, V9.

As shown in FIG. 6, spinal rods 34, 124 are attached with an apical portion of vertebrae V, and tether 22 and tether 28 are axially spaced along vertebrae V. Tether 22 and tether 28 are disposed in an offset arrangement with respect to rods 34, 124 along vertebrae V. Spinal rods 34, 124 are disposed in a substantially parallel arrangement along the apical portion of vertebrae V.

Figure 9:
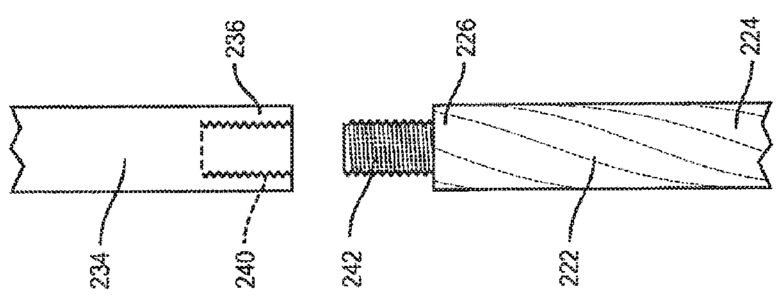
FIG. 9 is a side view of components of the system shown in FIG. 8.
Figure 8:
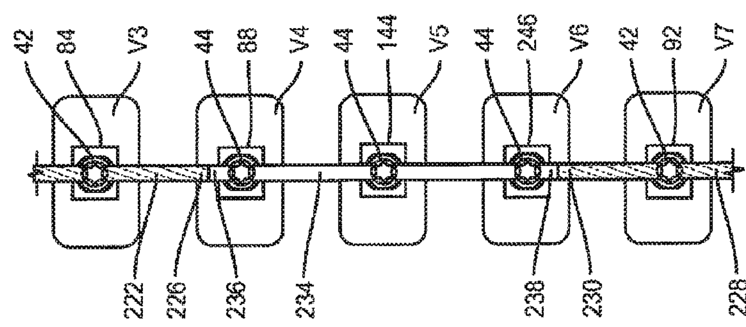
FIG. 8 is a plan view of components of one embodiment of a spinal correction system in accordance with the principles of the present disclosure disposed with vertebrae.

In one embodiment, as shown in FIGS. 8 and 9, spinal correction system 20, similar to the systems and methods described herein, includes a spinal rod 234, similar to the spinal rods described herein, and tethers 222, 228, similar to the tethers described herein.

Spinal rod 234 extends between ends 236, 238. End 236 includes a cavity 240 having an inner surface. The inner surface of cavity 240 includes a thread form configured for engagement and connection with an end of tether 222. End 238 includes a cavity (not shown), similar to end 236 above, having an inner surface. The inner surface of the cavity at end 238 includes a thread form configured for engagement and connection with an end of tether 228, discussed below.

Tether 222 includes a flange 242 extending from end 226. Flange 242 is threadably engageable with cavity 240 such that rod 234 and tether 222 are in axial alignment. Tether 228 includes a flange (not shown), similar to flange 242 described above, extending from end 230. The flange at end 230 is threadably engageable with the cavity of at end 238 of rod 234 such that rod 234 and tether 222 are in axial alignment. In some embodiments, the flange of tether 222 and/or tether 228 can be a rigid component, for example, those materials described herein, relative to the tether. System 20 includes plates 244, 246, similar to plate 88 discussed above. Tethers 222, 228 and spinal rod 234 can be fixed and/or locked, provisionally, removably and/or permanently. In some embodiments, end 236 and/or end 238 can include a flange, as described above, and end 226 and/or end 230 can include a surface defining a cavity, as described above, for threaded engagement with the flange and connection of rod 234 and tethers 222, 228.

Figure 10:
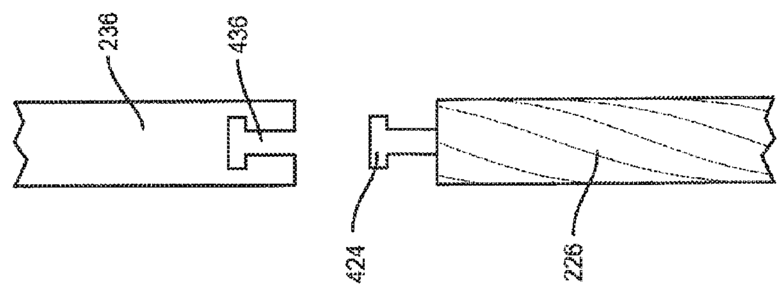
FIG. 10 is a plan view of components of one embodiment of a spinal correction system in accordance with the principles of the present disclosure.

In some embodiments, system 20 can alternatively connect and/or join the relatively rigid and non-rigid components of system 20, for example, to co-axially align spinal rod 234 and tethers 222, 228. For example, in one embodiment, as shown in FIG. 10, end 236 includes a cavity, such as, for example, a keyway 436 having an inner surface configured as a female mating part. The inner surface of keyway 436 is configured for engagement and connection with an end of tether 222. Tether 222 includes a key 424 configured as a male mating part extending from end 226. Key 424 is manipulated for lateral assembly with keyway 436 such that rod 234 and tether 222 are in co-axial alignment. The surface of key 424 and the surface that defines keyway 436 engage to prevent axial disengagement of tether 222 and rod 234. In some embodiments, end 236 can include a key, as described above, and end 226 can include a surface defining a keyway, as described above, for engagement with the key and connection of rod 234 and tether 222.

Figure 12:
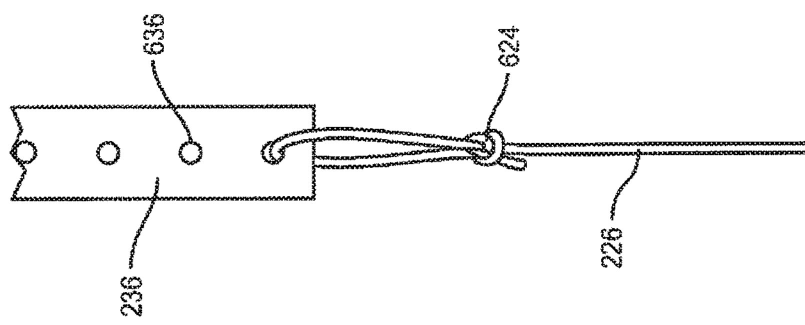
FIG. 12 is a plan view of components of one embodiment of a spinal correction system in accordance with the principles of the present disclosure.
Figure 11:
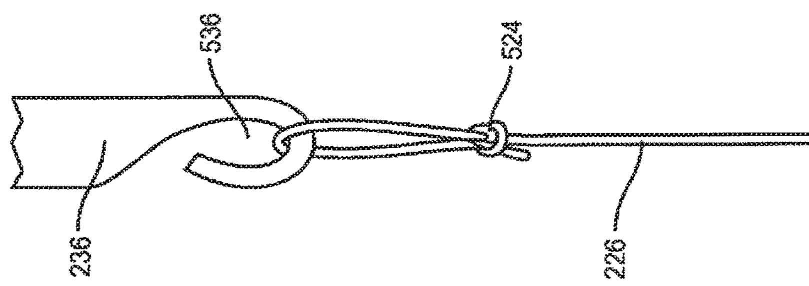
FIG. 11 is a plan view of components of one embodiment of a spinal correction system in accordance with the principles of the present disclosure.

In one embodiment, as shown in FIG. 11, end 236 includes a hook 536 having an arcuate configuration and end 226 includes a suture loop 524 to connect and/or join the relatively rigid and non-rigid components of system 20, for example, to co-axially align spinal rod 234 and tethers 222, 228. Loop 524 is configured to wrap around hook 536 such that loop 524 is removably connected with hook 536. In one embodiment, as shown in FIG. 12, end 236 includes a plurality of spaced apart through openings 636 and end 226 includes a suture loop 624 to connect and/or join the relatively rigid and non-rigid components of system 20, for example, to co-axially align spinal rod 234 and tethers 222, 228. Loop 624 is selectively disposed with one of openings 636 such that loop 524 is fixedly and/or permanently connected with end 236. In some embodiments, openings 636 are spaced at increments along end 236. In some embodiments, the incremental spacing allows for adjustment of the length of the tethers and/or rods. In some embodiments, end 236 can be cut to a desired length.

Pilot holes are made in vertebrae V for receiving bone fasteners 42, 44 that connect plates 84, 88, 244, 246, 92, tethers 222, 228 and spinal rod 234 with vertebrae V1-V9. In some embodiments, the sequence and/or order of connecting bone fasteners 42, 44, plates 84, 88, 244, 246, 92, tethers 222, 228 and spinal rod 234 with vertebrae V1-V9, may be variously arranged.

A pilot hole is made in vertebra V3 for receiving bone fastener 42 that connects tether 222 and plate 84 with vertebra V3. Plate 84 is removably engaged with a delivery instrument (not shown) and delivered along the surgical pathway. Plate 84 is delivered to a surgical site adjacent vertebra V3. Plate 84 is oriented for fixation with vertebra V3. Bone fastener 42 is inserted or otherwise engaged with vertebra V3 to fix an intermediate portion of tether 222 with plate 84 and vertebra V3. Bone fasteners 42 are similarly inserted or otherwise engaged with vertebrae V1, V2 to fix tether 222 with plate 84 and vertebrae V1, V2.

A pilot hole is made in vertebra V4 for receiving bone fastener 44. Tether 224 is fixed with spinal rod 234. Bone fastener 44 connects end 236 of rod 234 and plate 88 with vertebra V4. A pilot hole is made in vertebra V4 for receiving bone fastener 44 placed in axial alignment with bone fastener 42 of vertebrae V3. Bone fastener 44 connects end 236 of spinal rod 234 and plate 88 with vertebra V4. Plate 88 is removably engaged with a delivery instrument (not shown) and delivered along the surgical pathway. Plate 88 is delivered to a surgical site adjacent vertebra V4. Plate 88 is oriented for fixation with vertebra V4. Bone fastener 44 is inserted or otherwise engaged with vertebra V4 to fix end 236 with plate 88 and vertebra V4.

A pilot hole is made in vertebra V5 for receiving bone fastener 44. The pilot hole in vertebra V5 is disposed to connect spinal rod 234 in a selected alignment with bone fastener 44 attached to vertebra V4 and/or vertebra V6 along vertebrae V. Bone fastener 44 connects an intermediate portion of spinal rod 234 and plate 244 with vertebra V5. Plate 244 is removably engaged with a delivery instrument (not shown) and delivered along the surgical pathway. Plate 244 is delivered to a surgical site adjacent vertebra V5. Plate 244 is oriented for fixation with vertebra V5. Bone fastener 44 is inserted or otherwise engaged with vertebra V5 to fix an intermediate portion of spinal rod 234 with plate 244 and vertebra V5.

A pilot hole is made in vertebra V6 for receiving bone fastener 44. The pilot hole in vertebra V6 is disposed to connect spinal rod 234 in a selected alignment with bone fastener 44 attached to vertebra V5 along vertebrae V. The flange disposed on end 230 of tether 228 is engaged with end 238 of spinal rod 234. Bone fastener 44 connects end 238 of spinal rod 234 and plate 246 with vertebra V6. A pilot hole is made in vertebra V6 for receiving bone fastener 44 and is spaced in axial alignment with fastener 11 in vertebrae V5. Plate 246 is removably engaged with a delivery instrument (not shown) and delivered along the surgical pathway. Plate 246 is delivered to a surgical site adjacent vertebra V6. Plate 246 is oriented for fixation with vertebra V6. Bone fastener 44 is inserted or otherwise engaged with vertebra V6 to fix end 238 with plate 246 and vertebra V6.

A pilot hole is made in vertebra V7 for receiving bone fastener 42. The pilot hole in vertebra V1 is disposed to connect tether 228 in a selected alignment with bone fastener 44 attached to vertebra V6 along vertebrae V. Bone fastener 42 connects an intermediate portion of tether 228 and plate 92 with vertebra V7. Plate 92 is removably engaged with a delivery instrument (not shown) and delivered along the surgical pathway. Plate 92 is delivered to a surgical site adjacent vertebra V1. Plate 92 is oriented for fixation with vertebra VT. Bone fastener 68 is inserted or otherwise engaged with vertebra V to fix an intermediate portion of tether 28 with plate 92 and vertebra VT. Bone fasteners 42 are similarly inserted or otherwise engaged with vertebrae V8, V9 to fix tether 28 with plates 92 and vertebrae V8, V9.

As shown in FIG. 8, spinal rod 234 is attached with an apical portion of vertebrae V, and tether 222 and tether 228 are axially spaced along vertebrae V. Spinal rod 234 and tethers 222, 228 are disposed in a substantially coaxial arrangement along vertebrae V.

Figure 13:
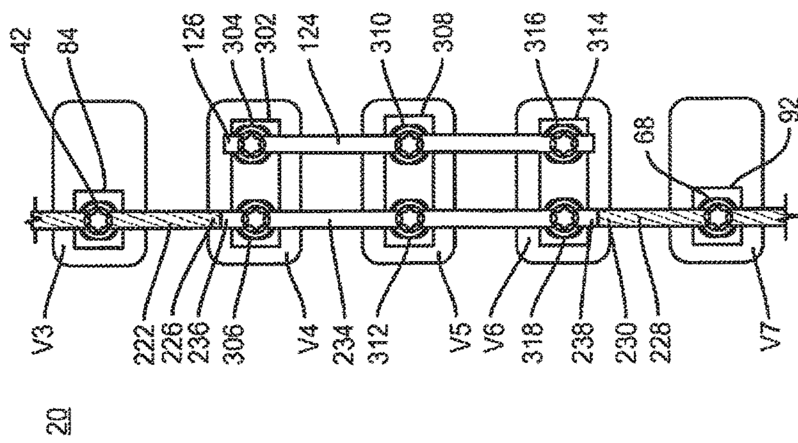
FIG. 13 is a plan view of components of one embodiment of a spinal correction system in accordance with the principles of the present disclosure disposed with vertebrae.

In one embodiment, as shown in FIG. 13, spinal correction system 20, similar to the systems and methods described herein, is employed with a lumbar section of vertebrae V. Spinal correction system 20 includes a plate 302, similar to the plate 66 described above. Plate 302 has a double plate configuration and includes an opening 304 configured for disposal of bone fastener 44 and an opening 306 configured for disposal of bone fastener 44. Opening 306 is spaced from opening 304 along the surface of plate 302 for alignment of spinal rods 234, 124, described above.

A plate 308, similar to the plate 302 described above, has a double plate configuration and includes an opening 310 configured for disposal of bone fastener 44 and an opening 312 configured for disposal of bone fastener 44. Opening 312 is spaced from opening 310 along the surface of plate 308 for alignment spinal rods 234, 124.

A plate 314, similar to the plate 302 described above, has a double plate configuration and includes an opening 316 configured for disposal of bone fastener 44 and an opening

318 configured for disposal of bone fastener 44. Opening 318 is spaced from opening 316 along the surface of plate 314 for alignment spinal rods 234, 124.

Pilot holes are made in vertebrae V for receiving bone fasteners 42, 44, 68 that connect plates 84, 302, 308, 314, 92, tethers 222, 228 and spinal rods 234, 124 with vertebrae V1-V9. In some embodiments, the sequence and/or order of connecting bone fasteners 42, 44, 68, plates 84, 302, 308, 314, 92, tethers 222, 228 and spinal rods 234, 124 with vertebrae V1-V9, may be variously arranged.

A pilot hole is made in vertebra V3 for receiving bone fastener 42 that connects tether 222 and plate 84 with vertebra V3. Plate 84 is removably engaged with a delivery instrument (not shown) and delivered along the surgical pathway. Plate 84 is delivered to a surgical site adjacent vertebra V3. Plate 84 is oriented for fixation with vertebra V3. Bone fastener 42 is inserted or otherwise engaged with vertebra V3 to fix an intermediate portion of tether 222 with plate 84 and vertebra V3. Bone fasteners 42 are similarly inserted or otherwise engaged with vertebrae V1, V2 to fix tether 222 with plate 84 and vertebrae V1, V2.

Pilot holes are made in vertebra V4 for receiving bone fasteners 44. Pilot holes in vertebra V4 are disposed to connect rods 234, 124 to vertebra V4 along vertebrae V to plate 302. Pilot holes are made in vertebra V4 for receiving bone fasteners 44 being spaced laterally from each other in vertebra V4. End 226 of tether 222 is threadably engaged with end 236 of spinal rod 234 in axial alignment. Bone fasteners 44 connect end 236 of rod 234 and end 126 of rod 124 and plate 302 with vertebra V4. Rod 124 is positioned offset from rod 234 and tether 222. Plate 302 is removably engaged with a delivery instrument (not shown) and delivered along the surgical pathway. Plate 302 is delivered to a surgical site adjacent vertebra V4. Plate 302 is oriented for fixation with vertebra V4. Bone fasteners 44 are inserted or otherwise engaged with vertebra V4 to fix end 236 and end 126 with plate 302 and vertebra V4.

Pilot holes are made in vertebra V5 for receiving bone fasteners 44. The pilot holes in vertebra V5 are disposed to connect spinal rods 234, 124 in a selected alignment with bone fasteners 44 attached to vertebra V4 and/or vertebra V6 along vertebrae V. Bone fasteners 44 connect an intermediate portion of spinal rods 234, 124 and plate 308 with vertebra V5. Plate 308 is removably engaged with a delivery instrument (not shown) and delivered along the surgical pathway. Plate 308 is delivered to a surgical site adjacent vertebra V5. Plate 308 is oriented for fixation with vertebra V5. Bone fasteners 44 are inserted or otherwise engaged with vertebra V5 to fix an intermediate portion of spinal rods 234, 124 with plate 308 and vertebra V5.

Pilot holes are made in vertebra V6 for receiving bone fasteners 44 being spaced laterally apart from each other along vertebrae V6. The pilot holes in vertebra V6 are disposed to connect spinal rods 234, 124 in a selected alignment with bone fasteners 44 attached to vertebra V5 along vertebrae V. Bone fasteners 44 connect end 238 of spinal rod 234, end 128 of spinal rod 124 and plate 314 with vertebra V6. End 230 of tether 228 is threadably engaged with end 238 of rod 234. Plate 314 is removably engaged with a delivery instrument (not shown) and delivered along the surgical pathway. Plate 314 is delivered to a surgical site adjacent vertebra V6. Plate 314 is oriented for fixation with vertebra V6. Bone fasteners 44 are inserted or otherwise engaged with vertebra V6 to fix ends 238, 128 with plate 314 and vertebra V6.

A pilot hole is made in vertebra V7 for receiving bone fastener 68. The pilot hole in vertebra V7 is disposed to connect tether 228 in an axial alignment with rod 234. Bone fastener 68 connects an intermediate portion of tether 228 and plate 92 with vertebra V7. Plate 92 is removably engaged with a delivery instrument (not shown) and delivered along the surgical pathway. Plate 92 is delivered to a surgical site adjacent vertebra V7. Plate 92 is oriented for fixation with vertebra W. Bone fastener 68 is inserted or otherwise engaged with vertebra V7 to fix an intermediate portion of tether 228 with plate 92 and vertebra V7. Bone fasteners 68 are similarly inserted or otherwise engaged with vertebrae V8, V9 to fix tether 228 with plates 92 and vertebrae V8, V9.

As shown in FIG. 13, spinal rods 234, 124 are attached in a side by side orientation with an apical portion of vertebrae V and disposed in a substantially parallel arrangement adjacent a lumbar region of vertebrae V, and tether 222 and tether 228 are disposed in a substantially co-axial arrangement with rod 234 along vertebrae V.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of treating a patient with a spinal disorder comprising:

attaching a first member to a first portion of vertebral tissue;

attaching a second member to a second portion of the vertebral tissue that is spaced apart from the first portion;

attaching a third member to an apical portion of the vertebral tissue along a portion of at least two vertebrae such that a first end of the third member is connected to a first transition and a second end of the third member is connected to a second transition, the first transition being attached to the first vertebral tissue and the second transition being attached to the second vertebral tissue, wherein the first portion, the second portion and the apical portion are on a convex side of a spine such that the members prevent growth of vertebrae on the convex side, while allowing for growth and adjustment on a concave side of the vertebrae.

2. A method as recited in claim 1, wherein attaching the first member comprises attaching the first member to the first transition and attaching the second member comprises attaching the second member to the second transition.

3. A method as recited in claim 1, wherein attaching the first member comprises attaching the first member to the first transition such that the first member is spaced apart from the third member and attaching the second member comprises attaching the second member to the second transition such that the second member is spaced apart from the third member.

4. A method as recited in claim 1, wherein:

attaching the third member comprises attaching the first end to a first bone fastener that extends through the first transition and attaching the second end to a second bone fastener that extends through the second transition;

attaching the first member comprises attaching the first member to a third bone fastener that extends through the first transition;

attaching the second member comprises attaching the second member to a fourth bone fastener that extends through the second transition; and the first and third bone fasteners are spaced apart from one another and the second and fourth bone fasteners are spaced apart from one another.

5. A method as recited in claim 1, wherein:

attaching the third member comprises attaching the first end to a first bone fastener that extends through the first transition and attaching the second end to a second bone fastener that extends through the second transition;

attaching the first member comprises attaching a first end of the first member to a third bone fastener that extends through the first transition and attaching a second end of the first member to a fourth bone fastener that extends through a third transition that is spaced apart from the first and second transitions;

attaching the second member comprises attaching a first end of the second member to a fifth bone fastener that extends through the second transition and attaching a second end of the second member to a sixth bone fastener that extends through a fourth transition that is spaced apart from the first, second and third transitions; and the first and third bone fasteners are spaced apart from one another and the second and fifth bone fasteners are spaced apart from one another.

6. A method as recited in claim 5, wherein the first transition includes a plate attached to a first vertebral level, the second transition includes a plate attached to a second vertebral level, the third transition includes a plate attached to a third vertebral level and the fourth transition includes a plate attached to a fourth vertebral level.

7. A method as recited in claim 1, wherein the first and second members each have a flexible configuration the third member has a non-flexible configuration.

8. A method as recited in claim 1, wherein the first and second members each include a tether and the third member includes a spinal rod.

9. A method as recited in claim 1, wherein the first and second members are resorbable.

10. A method as recited in claim 1, wherein at least one of the transitions include a plate.

11. A method as recited in claim 1, wherein the first transition includes a plate attached to a first vertebral level and the second transition includes a plate attached to a second vertebral level.

12. A method as recited in claim 1, wherein the first member and the second member are disposed in a substantially coaxial arrangement to define a first longitudinal axis and the third member defines a second longitudinal axis spaced apart and disposed in a substantially parallel orientation relative to the first longitudinal axis.

13. A method as recited in claim 1, wherein the third member includes a pair of spaced apart spinal rods.

14. A method as recited in claim 1, wherein the first member and the second member are disposed in a substantially coaxial arrangement to define a first longitudinal axis and the third member defines a second longitudinal axis spaced apart and disposed in a substantially parallel orientation relative to the first longitudinal axis.

15. A method of treating a patient with a spinal disorder comprising:

attaching a first longitudinal element to a first portion of vertebral tissue;

attaching a second longitudinal element to a second portion of vertebral tissue that is spaced apart from the first portion;

attaching at least one intermediate longitudinal element having a non-flexible configuration relative to the first and second longitudinal elements to an apical portion of the vertebral tissue along a portion of at least a first vertebra and a second vertebra such that a first end of the at least one intermediate longitudinal element is connected to a first plate and a second end of the at least one intermediate longitudinal element is connected to a second plate, the first plate being attached to the first vertebral tissue and the second plate being attached to the second vertebral tissue, wherein the first and second longitudinal elements each include a tether and the at least one intermediate longitudinal element includes a spinal rod.

16. A method as recited in claim 15, wherein the first longitudinal element and the second longitudinal element are disposed in a substantially coaxial arrangement to define a first longitudinal axis and the intermediate element defines a second longitudinal axis spaced apart and disposed in a substantially parallel orientation relative to the first longitudinal axis.

17. A method as recited in claim 15, wherein the first and second longitudinal elements each include a tether and the at least one intermediate longitudinal element includes a spinal rod, the first longitudinal element having varying degrees of flexibility relative to the second longitudinal element.

18. A method as recited in claim 15, wherein the first and second longitudinal elements each have a flexible configuration the third member has a non-flexible configuration, the flexible configurations each including movement in a lateral direction and preventing extension in an axial direction.

19. A method as recited in claim 15, wherein the tethers each have a flexible configuration.

20. A method of treating a patient with a spinal disorder comprising:

attaching a first plate to a first vertebra by positioning first and second bone fasteners through the first plate and into the first vertebra such that the first and second bone fasteners are spaced apart from one another;

attaching a second plate to a second vertebra that is spaced apart from the first vertebra by positioning third and fourth bone fasteners through the second plate and into the second vertebra such that the third and fourth bone fasteners are spaced apart from one another;

attaching a first longitudinal element to the first bone fastener;

attaching a second longitudinal element to the third bone fastener such that the second longitudinal element is coaxial with the first longitudinal element along a longitudinal axis; and attaching at least one intermediate longitudinal element having a non-flexible configuration relative to the first and second longitudinal elements to the second and fourth bone fasteners such that the at least one intermediate longitudinal element is parallel to the longitudinal axis and offset from the longitudinal axis.

* * * * *

UNITED STATES PATENT AND TRADEMARK OFFICE

CERTIFICATE OF CORRECTION

PATENT NO. : 10,045,796 B2
APPLICATION NO. : 14/965412
DATED : August 14, 2018
INVENTOR(S) : Powers et al.

It is certified that error appears in the above-identified patent and that said Letters Patent is hereby corrected as shown below:

In Fig. 8, Sheet 4 of 5, delete Tag “144” and insert Tag -- 244 --, therefor.

In Column 1, Line 8, delete “2013,” and insert -- 2013, now Pat. No. 9,237,907, --, therefor.

In Column 1, Line 9, delete “reference, in” and insert -- reference in --, therefor.

In Column 6, Line 45, delete “between an ends” and insert -- between ends --, therefor.

In Column 11, Line 39, delete “vertebra V1” and insert -- vertebra V7 --, therefor.

In Column 16, Line 22, delete “fastener 11” and insert -- fastener 44 --, therefor.

In Column 16, Line 30, delete “vertebra V1” and insert -- vertebra V7 --, therefor.

In Column 16, Line 37, delete “vertebra V1.” and insert -- vertebra V7. --, therefor.

In Column 16, Line 38, delete “vertebra VT.” and insert -- vertebra V7. --, therefor.

In Column 16, Line 39, delete “vertebra V” and insert -- vertebra V7 --, therefor.

In Column 16, Line 40, delete “vertebra VT.” and insert -- vertebra V7. --, therefor.

In Column 18, Line 7, delete “vertebra W.” and insert -- vertebra V7. --, therefor.

Signed and Sealed this
Fourth Day of December, 2018

Andrei Iancu
*Director of the United States Patent and Trademark Office*